United States Patent
Itai

(10) Patent No.: US 9,931,083 B2
(45) Date of Patent: Apr. 3, 2018

(54) IMAGE DISPLAY APPARATUS AND PROGRAM

(71) Applicant: FUJIFILM Corporation, Tokyo (JP)

(72) Inventor: Yoshinori Itai, Tokyo (JP)

(73) Assignee: FUJIFILM Corporation, Minato-Ku, Tokyo (JP)

( * ) Notice: Subject to any disclaimer, the term of this patent is extended or adjusted under 35 U.S.C. 154(b) by 460 days.

(21) Appl. No.: 14/624,949

(22) Filed: Feb. 18, 2015

(65) Prior Publication Data
US 2015/0157280 A1 Jun. 11, 2015

Related U.S. Application Data

(63) Continuation of application No. PCT/JP2013/004630, filed on Jul. 31, 2013.

(30) Foreign Application Priority Data

Aug. 21, 2012 (JP) .................................. 2012-182323

(51) Int. Cl.
*G09G 5/14* (2006.01)
*A61B 5/00* (2006.01)
(Continued)

(52) U.S. Cl.
CPC ............ *A61B 5/7425* (2013.01); *A61B 5/055* (2013.01); *A61B 6/032* (2013.01); *A61B 6/463* (2013.01);
(Continued)

(58) Field of Classification Search
CPC ........... A61B 6/03; A61B 6/032; A61B 6/463; A61B 6/467; A61B 6/486; A61B 6/5235;
(Continued)

(56) References Cited

U.S. PATENT DOCUMENTS

| 8,334,878 B2 | 12/2012 | Moriya et al. | |
| 2010/0076311 A1* | 3/2010 | Tabar | A61B 8/0825 600/443 |
| 2010/0231605 A1* | 9/2010 | Moriya | G06F 19/321 345/619 |

FOREIGN PATENT DOCUMENTS

| JP | 2005-124895 A | 5/2005 |
| JP | 2008-043524 A | 2/2008 |

(Continued)

OTHER PUBLICATIONS

Communication dated Apr. 14, 2016 from the European Patent Office issued in corresponding Application No. 13831778.9.
(Continued)

*Primary Examiner* — Elmer Chao
(74) *Attorney, Agent, or Firm* — Sughrue Mion, PLLC

(57) ABSTRACT

A linked switching partial area and a non-linked switching partial area are set in at least one display area in which a tomogram is to be displayed. When an input operation giving an instruction to switch the tomogram is performed in the non-linked switching partial area, only the image displayed in the display area is switched. When the input operation is performed in the linked switching partial area, the image displayed in the display area is switched and an image displayed in each of the other display area or areas is also switched in a linked manner.

4 Claims, 2 Drawing Sheets

(51) Int. Cl.
  *A61B 5/055* (2006.01)
  *A61B 6/03* (2006.01)
  *A61B 6/00* (2006.01)
  *G06F 19/00* (2018.01)
  *G06T 19/00* (2011.01)
  *A61B 8/13* (2006.01)
  *A61B 8/00* (2006.01)
  *A61B 8/08* (2006.01)

(52) U.S. Cl.
  CPC .............. *A61B 6/467* (2013.01); *A61B 6/469* (2013.01); *A61B 6/486* (2013.01); *A61B 6/5235* (2013.01); *A61B 8/13* (2013.01); *A61B 8/463* (2013.01); *G06F 19/321* (2013.01); *G06F 19/3406* (2013.01); *G06T 19/00* (2013.01); *A61B 5/748* (2013.01); *A61B 5/7435* (2013.01); *A61B 6/5247* (2013.01); *A61B 8/5261* (2013.01); *G06T 2219/028* (2013.01)

(58) Field of Classification Search
  CPC ..... A61B 6/469; A61B 6/5247; A61B 5/7425; A61B 5/055; A61B 5/7435; A61B 5/748; A61B 8/13; A61B 8/463; A61B 8/5261; G06T 2200/24; G06T 2207/10072; G06T 2207/20212; G06T 2207/30004; G06T 7/0014; G06T 7/30; G06T 7/38; G06T 2219/028; G06F 19/321; G06F 19/3406; G06F 19/00
  See application file for complete search history.

(56) References Cited

FOREIGN PATENT DOCUMENTS

| | | |
|---|---|---|
| JP | 2008-090101 A | 4/2008 |
| JP | 2009-005906 A | 1/2009 |

OTHER PUBLICATIONS

Communication dated Oct. 20, 2015 from the Japanese Patent Office in counterpart application No. 2012-182323.

International Search Report of PCT/JP2013/004630 dated Oct. 22, 2013.

\* cited by examiner

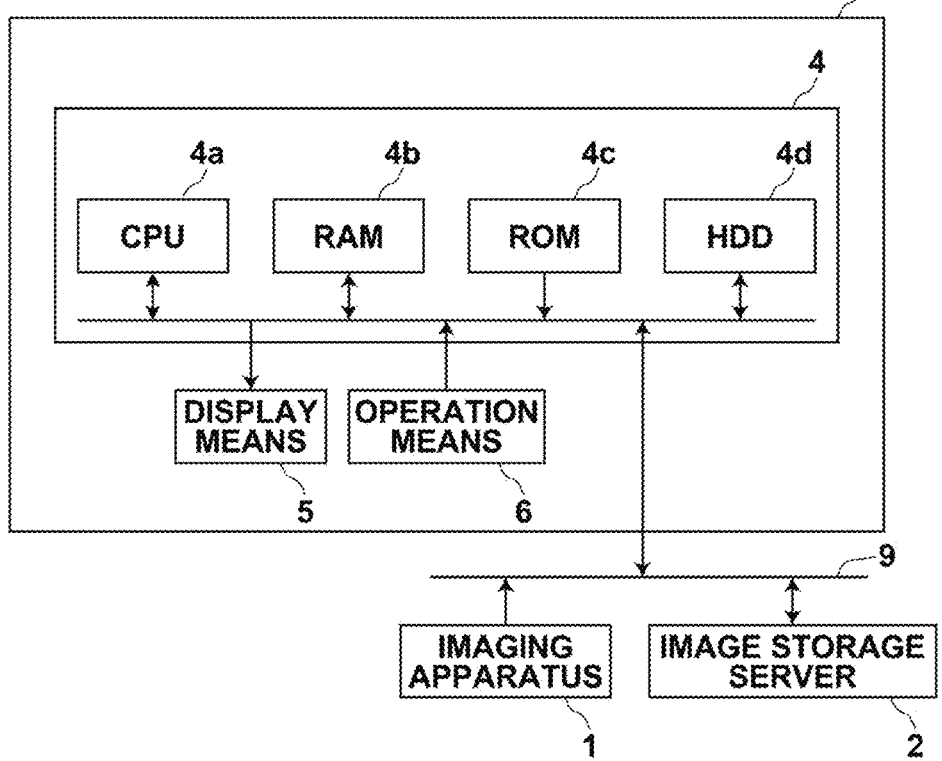
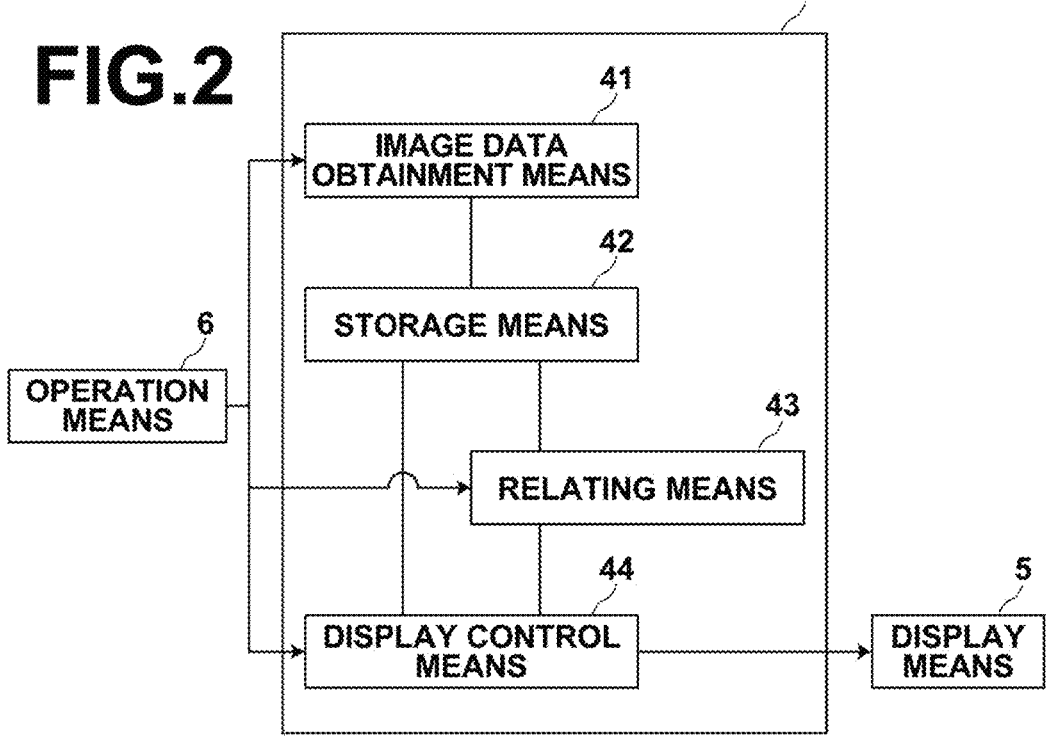

IMAGE DISPLAY APPARATUS AND PROGRAM

CROSS-REFERENCE TO RELATED APPLICATIONS

This application is a Continuation of PCT International Application No. PCT/JP2013/004630 filed on Jul. 31, 2013, which claims priority under 35 U.S.C. § 119(a) to Japanese Patent Application No. 2012-182323 filed on Aug. 21, 2012. Each of the above applications is hereby expressly incorporated by reference, in its entirety, into the present application.

BACKGROUND OF THE INVENTION

Field of the Invention

The present invention relates to an image display apparatus that obtains a tomogram from each of two or more image groups each including a series of tomograms, and between which tomograms are related to each other, and that displays the obtained tomograms arranged on a display screen, and also to an image display program used in such an apparatus.

Description of the Related Art

Cases where a series of tomograms of a patient is obtained, for example, along the body axis of the patient by an imaging apparatus, such as a CT apparatus, an MRI apparatus and an ultrasonic diagnosis apparatus, and medical diagnosis is performed by using the tomograms have increased in recent years.

Japanese Unexamined Patent Publication No. 2005-124895 (Patent Document 1) proposes a technique used in observation of a temporal change of a diseased part of a patient. In the technique, each of an image group of plural tomograms obtained on that day by imaging a predetermined range including the diseased part by using an imaging apparatus and an image group obtained in the past by imaging about the same region of the same patient is loaded. Further, a tomogram of that day and a tomogram of the past representing about the same slice position are related to each other by performing position matching between the image groups. Further, the tomograms related to each other are displayed in such a manner to be arranged on a display screen. Further, Japanese Unexamined Patent Publication No. 2008-043524 (Patent Document 2) proposes switching display by an input operation by a user that gives an instruction to switch tomograms, or automatically in such a manner that each of the tomograms related to each other is sequentially displayed at the same timing on the display device.

SUMMARY OF THE INVENTION

Meanwhile, when tomograms obtained from plural image groups, respectively, as described above, are displayed in such a manner to be arranged, and comparative observation is performed on the displayed tomograms, an operation of switching display of tomograms while changing the mode of switching display of tomograms displayed in respective display areas from a linked switch display mode to a non-linked switch display mode, or vice versa needs to be performed, for example, when a user wants to check whether tomograms are correctly related to each other.

At this time, for example, a button for receiving an instruction to change link/non-link may be arranged outside an image display area, and link/non-link may be changed based on an operation by a user at the button. However, in this method, a complicated operation, such as clicking after moving a cursor to the position of the button each time, is necessary, and the method is inconvenient. Meanwhile, each of the aforementioned patent documents includes descriptions about linked switch display, but is silent about changing link/non-link.

In view of the foregoing circumstances, it is an object of the present invention to provide an image display apparatus and program in which a user can more easily change link/non-link of switching display between plural display areas in which tomograms are displayed when the tomograms obtained from plural image groups, respectively, are observed by being displayed in such a manner to be arranged.

An image display apparatus of the present invention includes a display control means that obtains a tomogram from each of two or more image groups each including a series of tomograms, and between which tomograms are related to each other, and that displays the obtained tomograms arranged on a display screen, and an input operation receiving means that receives, in at least one of plural display areas on the display screen in which the tomograms are displayed by the display control means, an input operation that gives an instruction to switch the tomogram displayed in the at least one of the plural display areas. The display control means sets a linked switching partial area and a non-linked switching partial area in the at least one of the plural display areas in which the input operation is to be received by the input operation receiving means. The display control means switches only the tomogram displayed in the display area in which the input operation has been performed to a tomogram succeeded by or succeeding the displayed tomogram in the same image group when the input operation received by the input operation receiving means has been performed in the non-linked switching partial area. The display control means switches the tomogram displayed in the display area in which the input operation has been performed to the tomogram succeeded by or succeeding the displayed tomogram in the same image group and also switches the tomogram displayed in each of the other display area or areas to a tomogram that is included in the same image group as the tomogram displayed in each of the other display area or areas and related to the tomogram displayed after switching in the display area in which the input operation has been performed when the input operation received by the input operation receiving means has been performed in the linked switching partial area.

An image display program of the present invention is an image display program for causing a computer to function as a display control means that obtains a tomogram from each of two or more image groups each including a series of tomograms, and between which tomograms are related to each other, and that displays the obtained tomograms arranged on a display screen, and an input operation receiving means that receives, in at least one of plural display areas on the display screen in which the tomograms are displayed by the display control means, an input operation that gives an instruction to switch the tomogram displayed in the at least one of the plural display areas. The display control means sets a linked switching partial area and a non-linked switching partial area in the at least one of the plural display areas in which the input operation is to be received by the input operation receiving means. The display control means switches only the tomogram displayed in the display area in which the input operation has been performed to a tomogram succeeded by or succeeding the displayed tomogram in the same image group when the input operation received by the input operation receiving means has been performed in the non-linked switching partial area. The display control means switches the tomogram displayed in the display area in which the input operation has been performed to the tomogram succeeded by or succeeding the displayed tomogram in the same image group and also switches the tomogram displayed in each of the other display area or areas to a tomogram that is included in the same image group as the tomogram displayed in each of the other display area or areas and related to the tomogram displayed after switching in the display area in which the input operation has been performed when the input operation received by the input operation receiving means has been performed in the linked switching partial area.

Here, in the two or more image groups, all the tomograms in one of the image groups may be related to all the tomograms in the other image group or groups. Alternatively, a part of the tomograms in one of the image groups may be related to a part or all of the tomograms in the other image group or groups. At this time, for example, tomograms representing about the same slice position of a subject may be related to each other.

Further, the number of a tomogram or tomograms in another image group related to a tomogram in an image group may be one, or two or more.

Further, a tomogram may be obtained from each of two or more image groups, and a tomogram may be displayed on a display screen. Alternatively, one tomogram produced from two or more successive tomograms may be displayed.

Further, switching the tomogram to a tomogram that is related to the tomogram displayed after switching means switching to a tomogram that is included in the same image group as the tomogram to be switched and related to the tomogram displayed after switching when the number of tomograms that is included in the same group as the tomogram to be switched and related to the tomogram displayed after switching is one. When the number of tomograms that are included in the same image group as the tomogram to be switched and related to the tomogram displayed after switching is two or more, switching to one of the tomograms or to a tomogram produced from the two or more tomograms, such as an averaged image of the two or more tomograms, is meant.

In the image display apparatus and the image display program of the present invention, the display control means may set, as the non-linked switching partial area, an area including at least a part of a region of interest in a tomogram displayed in a display area in which the non-linked switching partial area is to be set.

Further, the display control means may have a function of displaying a boundary of the set non-linked switching partial area on the display screen.

When a tomogram is obtained from each of three or more image groups, and the tomograms are displayed in such a manner to be arranged on a display screen, the image display apparatus and program of the present invention may be applied to each of the three or more image groups. Alternatively, the image display apparatus and program may be applied to at least two of the three or more image groups.

According to the image display apparatus and an image display program of the present invention, when a tomogram is obtained from each of two or more image groups each including a series of tomograms, and between which tomograms are related to each other, and the obtained tomograms are displayed in such a manner to be arranged on a display screen, a linked switching partial area and a non-linked switching partial area are set in at least one display area in which a tomogram is to be displayed. An input operation that gives an instruction to switch the tomogram displayed in the display area is received in the display area. Further, only the tomogram displayed in the display area in which the input operation has been performed is switched to a tomogram succeeded by or succeeding the displayed tomogram in the same image group when the input operation has been performed in the non-linked switching partial area. When the input operation has been performed in the linked switching partial area, the tomogram displayed in the display area in which the input operation has been performed is switched to the tomogram succeeded by or succeeding the displayed tomogram in the same image group, and the tomogram displayed in each of the other display area or areas is switched to a tomogram that is included in the same image group as the tomogram displayed in each of the other display area or areas and related to the tomogram displayed after switching in the display area in which the input operation has been performed. Therefore, a user can easily change link/non-link of switching display between plural display areas in which tomograms are displayed only by shifting a position at which an input operation is performed from one of a linked switching partial area and a non-linked switching partial area that are set in the same display area to the other one. Therefore, the convenience of the user is improved.

Ordinarily, when switching display is performed in such a manner that tomograms are linked with each other, a visual range of a user tends to become wide in such a manner that the whole area of plural tomograms the display of which is switched is observable. However, when switching display is performed in such a manner that tomograms are not linked with each other, the visual range of the user tends to become narrow in such a manner that observation is concentrated especially in a region of interest in the tomogram to be switched. Therefore, in the image display apparatus and the image display program of the present invention, when an area including at least a part of a region of interest in a tomogram displayed in a display area is set as the non-linked switching partial area, a user can change link/non-link of switching display by a more instinctive operation. Therefore, the convenience of the user is improved.

Further, in the image display apparatus and the image display program of the present invention, when a boundary of a non-linked switching partial area is displayed on the display screen, a user can determine a position at which an input operation is to be performed while recognizing the range of the non-linked switching partial area. Therefore, an operation for changing link/non-link of switching display is performed more accurately.

BRIEF DESCRIPTION OF THE DRAWINGS

FIG. 1 is a schematic block diagram illustrating the configuration of an image processing system;

FIG. 2 is a functional block diagram illustrating the function of an image display apparatus.

DESCRIPTION OF THE PREFERRED EMBODIMENTS

Figure 3:
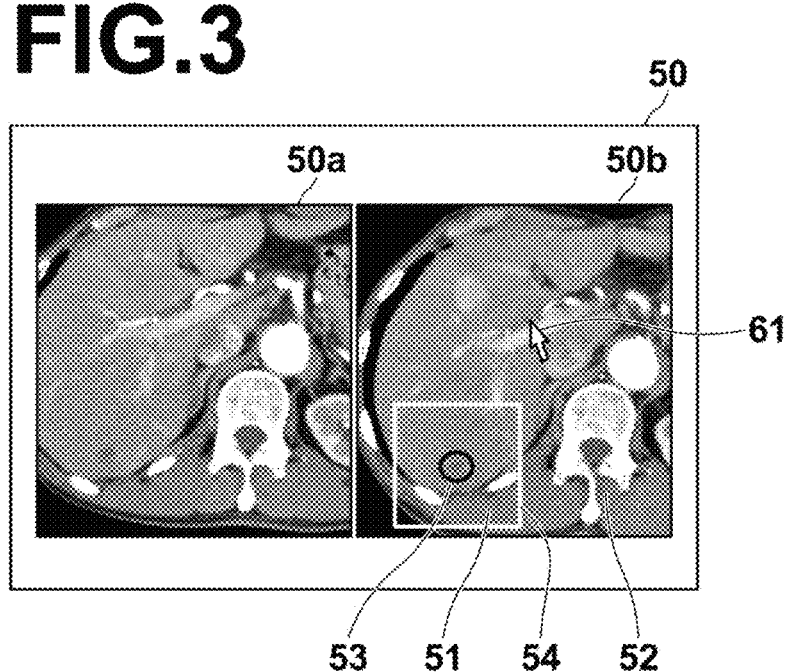
FIG. 3 is a diagram illustrating an example of a display screen displayed on a display means.

Next, with reference to drawings, an embodiment of the present invention will be described. FIG. 1 is a schematic block diagram illustrating the configuration of an image processing system. As illustrated in FIG. 1, in this system, an imaging apparatus 1, an image storage server 2 and an image display apparatus 3 are connected to each other through a network 9 in such a manner that they can communicate with each other.

The imaging apparatus 1 obtains an image group including plural tomograms succeeding in a predetermine direction by imaging a subject. Specifically, the imaging apparatus 1 is a CT apparatus, an MRI apparatus, an ultrasonic diagnosis apparatus, and the like. The imaging apparatus 1 obtains plural tomograms succeeding, for example, along the body axis of a subject. The image storage server 2 is a computer that stores the image group obtained by the imaging apparatus 1 in an image database, and manages the image group. The image storage server 2 includes a large capacity external storage device and database management software.

The image display apparatus 3 is a computer (which may be a smartphone or a tablet computer) that obtains an image from the imaging apparatus 1 or the image storage server 2, and displays the image based on a request by a user. An apparatus body 4, in which a CPU and the like is stored, a display means 5 for displaying images, and an operation means 6 (an input operation receiving means) for receiving an input operation by a user are provided in the image display apparatus 3.

The display means 5 may be any means as long as the means has a display function. For example, a liquid crystal display, a CRT, a touch panel, a touch screen and the like are appropriately usable. The operation means 6 may be any means as long as the means has a function of receiving an input operation by a user. For example, a mouse, a keyboard, a touch pad and the like are appropriately usable. Further, a touch pen and a display that receives an operation of the touch pen, a touch panel, a touch screen and the like, which have also a display function, may be used as a means having both of the function of the display means 5 and the function of the operation means 6.

In the apparatus body 4, CPU 4a, RAM 4b, ROM 4c and HDD 4d, which are connected to each other through bus lines, are provided. The CPU 4a performs various kinds of control processing and operation processing based on programs stored in the ROM 4c and HDD 4d by using the RAM 4b as a temporary recording area. The HDD 4d stores various programs including the image display program of the present invention and data.

FIG. 2 is a functional block diagram illustrating the function of the image display apparatus 3. As illustrated in FIG. 2, the apparatus body 4 of the image display apparatus 3 functions as an image data obtainment unit 41, a storage means 42, a relating means 43 and a display control means 44 when the CPU 4a performs data processing by the programs stored in the HDD 4d.

The image data obtainment means 41 obtains image data from the imaging apparatus 1 and the image storage server 2 based on a request from a user. For example, the image data obtainment means 41 receives an input by a user that gives an instruction to display a comparative observation screen by specifying plural image groups on which comparative observation is to be performed. Further, the image data obtainment means 41 obtains image data in the specified plural image groups from the imaging apparatus 1 and the image storage server 2. The image data obtained by the image data obtainment means 41 are stored in the storage means 42.

The storage means 42 stores data in the HDD 4d and reads data from the HDD 4d. The storage means 42 is accessed by the image data obtainment means 41, the relating means 43 and the display control means 44, and data are read out from the storage means 42 and written in the storage means 42.

The relating means 43 reads out plural image groups on which comparative observation is to be performed from the storage means 42. Further, the relating means 43 relates tomograms representing about the same slice position to each other between the image groups by performing position matching between the image groups. Specifically, the relating means 43 relates each tomogram in each image group to a tomogram in the other group or groups representing about the same slice position, and obtains information representing the corresponding relationship. Here, the information representing the corresponding relationship may be information representing a corresponding relationship between the tomograms, itself. The information is sufficient as long as the corresponding relationship between the tomograms is derivable from the information. The information representing the corresponding relationship obtained by the relating means 43 is stored in the storage means 42.

The relating means 43 reads, for example, two image groups on which comparative observation is to be performed from the storage means 42. Further, the relating means 43 generates three-dimensional images from plural tomograms included in the image groups, respectively. The relating means 43 can obtain, as the information representing the corresponding relationship between the tomograms, image deformation amounts $WAB(xa)$, $WBA(xb)$ for deforming each of the three-dimensional images so as to be most matched with the other three-dimensional image by performing non-rigid registration on generated two three-dimensional images A, B. Here, $xa$ represents a voxel in three-dimensional image A, and $WAB(xa)$ represents a deformation amount of voxel $xa$ for deforming three-dimensional image A so as to be most matched with three-dimensional image B. Further, $xb$ represents a voxel in three-dimensional image B, and $WBA(xb)$ represents a deformation amount of voxel $xb$ for deforming three-dimensional image B so as to be most matched with three-dimensional image A. Accordingly, each of the tomograms from which three-dimensional A is generated is related to a tomogram or two or more tomograms of three-dimensional image B that are identified based on the position of the tomogram or an image deformation amount.

The display control means 44 receives an input by a user that gives an instruction to display a comparative observation screen by specifying plural image groups on which comparative observation is to be performed. Further, the display control means 44 obtains a tomogram from each of the plural image groups on which comparative observation is to be performed, and displays the obtained tomograms arranged on a display screen of the display means 5.

FIG. 3 is a diagram illustrating an example of a display screen 50 displayed on the display means 5. As illustrated in FIG. 3, display areas corresponding to respective image groups are provided in the display screen 50, and tomograms obtained from the image groups are displayed in the display areas. In the example illustrated in FIG. 3, two display areas 50a, 50b are provided to display tomograms obtained from two image groups, respectively, on which comparative observation is to be performed.

The display control means 44 may perform initial display by obtaining, with reference to information representing a corresponding relationship stored in the storage means 23, arbitrary tomograms representing about the same slice position from plural image groups. For example, the display control means 44 may set a base image group in plural image groups, and obtain a tomogram including a position specified by a user or the position of a lesion detected by the user or a computer-aided diagnosis (CAD) system from the image group. Further, the display control means 44 may display the obtained tomogram in a display area corresponding to the image group. The display control means 44 may also obtain a tomogram or tomograms in each of the other image group or groups related to the tomogram, and display the obtained tomogram or tomograms in a display area or areas corresponding to them.

Further, when an input operation that gives an instruction to switch tomograms (hereinafter, referred to as "a paging operation"), such as a mouse wheel operation and a key operation, is received by the operation means 6 in at least one of plural display areas in which tomograms are displayed, the display control means 44 switches display of the tomogram only in the display area in which the input operation has been received or in all the display areas.

The display control means 44 sets a linked switching partial area and a non-linked switching partial area in at least one display area in which the input operation is to be received by the operation means 6. The display control means 44 switches only the tomogram displayed in the display area in which the input operation has been performed to a tomogram succeeded by or succeeding the displayed tomogram in the same image group when the input operation has been performed in the non-linked switching partial area. The display control means 44 switches the tomogram displayed in the display area in which the input operation has been performed to the tomogram succeeded by or succeeding the displayed tomogram in the same image group and also switches the tomogram displayed in each of the other display area or areas to a tomogram that is included in the same image group as the tomogram displayed in each of the other display area or areas and related to the tomogram displayed after switching in the display area in which the input operation has been performed when the input operation has been performed in the linked switching partial area.

For example, in the display screen 50 illustrated in FIG. 3, paging operations are receivable in both of the two display areas 50a, 50b, respectively, and a non-linked switching partial area 51 and a linked switching partial area 52 are set in the display area 50b. Then, when an input operation has been performed in the display area 50b, judgment is made as to whether the input operation has been formed in the linked switching partial area 52 or in the non-linked switching partial area 51. Further, display may be switched, based on the judgment result, only in the display area 50b, which is one of the display areas, or in both of the display areas 50a, 50b.

Specifically, when a user performs a paging operation after moving a mouse cursor 61 to the non-linked switching partial area 51 in the display area 50b, only the tomogram displayed in the display area 50b is switched to a tomogram succeeded by or succeeding the displayed tomogram in the same image group. In contrast, when the user performs a paging operation after moving the mouse cursor 61 to the linked switching partial area 52 in the display area 50b, the tomogram displayed in the display area 50b is switched to the tomogram succeeded by or succeeding the displayed tomogram in the same image group and also the tomogram displayed in the display area 50a is switched to a tomogram that is included in the same image group as the tomogram displayed in the display area 50a and related to the tomogram displayed after switching in the display area 50b. Further, when the user performs a paging operation after moving the mouse cursor 61 to the display area 50a, the tomogram displayed in the display area 50a is switched to a tomogram succeeded by or succeeding the displayed tomogram in the same image group and also the tomogram displayed in the display area 50b is switched to a tomogram that is included in the same image group as the tomogram displayed in the display area 50b and related to the tomogram displayed after switching in the display area 50a.

The display control means 44 may set each of the linked switching partial area and the non-linked switching partial area at an arbitrary position in a display area and in an arbitrary size. The display control means 44 may set the linked switching partial area and the non-linked switching partial area next to each other, or at positions away from each other. Further, the linked switching partial area and the non-linked switching partial area may be set at predetermined fixed positions in the display area, respectively. Alternatively, the linked switching partial area and the non-linked switching partial area may be set at positions specified by the user, or positions determined by the position of a lesion detected by the user or the computer-aided diagnosis system.

For example, an area that has a predetermined size and includes at least a part of a region of interest in a tomogram displayed in the display area may be set as the non-linked switching partial area. It is desirable that an area including the whole region of interest and the vicinity thereof is set as the non-linked switching partial area. It is desirable that the size of the non-linked switching partial area is about ⅙ through ¼ of the display area. Further, an area other than the non-linked switching partial area may be set as the linked switching partial area. At this time, the display control means 44 may control display/non-display of a boundary of the non-linked switching partial area in the display screen. It is desirable that whether the boundary of the non-linked switching partial area is displayed or not is arbitrarily selectable by a user.

In the example illustrated in FIG. 3, a rectangular area with its center located approximately at the position of a region 53 of interest in the tomogram displayed in the display area 50b is set as the non-linked switching partial area 51. Further, an area other than the non-linked switching partial area 51 is set as the linked switching partial area 52. Further, a boundary 54 of the non-linked switching partial area 51 is displayed.

The image processing system of the embodiment of the present invention is configured as described above. Therefore, in the image processing system, when a tomogram is obtained from each of two or more image groups each including a series of tomograms on which comparative observation is to be performed, and the obtained tomograms are displayed in such a manner to be arranged on a display screen, a linked switching partial area and a non-linked switching partial area are set in at least one display area in which a tomogram is displayed. An input operation that gives an instruction to switch the tomogram displayed in the display area is received in the display area. Then, only the tomogram displayed in the display area in which the input operation has been performed is switched to a tomogram succeeded by or succeeding the displayed tomogram in the same image group when the input operation has been performed in the non-linked switching partial area. When the input operation has been performed in the linked switching partial area, the tomogram displayed in the display area in which the input operation has been performed is switched to the tomogram succeeded by or succeeding the displayed tomogram in the same image group, and the tomogram displayed in each of the other display area or areas is switched to a tomogram that is included in the same image group as the tomogram displayed in each of the other display area or areas and related to the tomogram displayed after switching in the display area in which the input operation has been performed. Therefore, a user can perform comparative observation while changing link/non-link of switching display between plural display areas in which tomograms are displayed by a simple operation of shifting a position at which an input operation is performed from one of a linked switching partial area and a non-linked switching partial area that are set in the same display area to the other one.

The embodiment was described by using, as an example, a case in which the number of image groups on which comparative observation is to be performed is two. When comparative observation is performed on three or more image groups, the various technical modes used in comparative observation of two image groups, as described above, are adoptable in a similar manner.

The embodiment was described by using, as an example, a case in which paging operations are received in all the display areas in which tomogram are displayed. Alternatively, the paging operation may be received only in at least one display area.

The embodiment was described by using, as an example, a case in which a linked switching partial area and a non-linked switching partial area are set only in one display area. When the number of areas in which paging operations is to be received is two or more, a linked switching partial area and a non-linked switching partial area may be set in a part or all of the areas.

In the embodiment, a case in which the relating means 43 is provided in the image display apparatus 4, and processing for relating tomograms to each other is performed in the image display apparatus 4 was described. However, when such processing has been already performed by another computer or the like, and the result of processing is retrievable, the relating means 43 is not always necessary in the configuration of the system.

What is claimed is:

1. An image display apparatus comprising:
    a processor configured to:
        obtain a tomogram from each of two or more image groups each including a series of tomograms, and between which tomograms are related to each other;
        display the obtained tomograms arranged on a display screen; and
        set a linked switching partial area and a non-linked switching partial area in at least one of the plurality of display areas in which the tomograms are displayed and an input operation is to be received by an input operation receiving unit;
        when the input operation received by the input operation receiving unit has been performed in the non-linked switching partial area, switch only the tomogram displayed in the display area in which the input operation has been performed to a tomogram succeeded by or succeeding the displayed tomogram in the same image group;
        when the input operation received by the input operation receiving unit has been performed in the linked switching partial area, switch the tomogram displayed in the display area in which the input operation has been performed to the tomogram succeeded by or succeeding the displayed tomogram in the same image group and also switch the tomogram displayed in each of the other display area or areas to a tomogram that is included in the same image group as the tomogram displayed in each of the other display area or areas and related to the tomogram displayed after switching in the display area in which the input operation has been performed; and
        set, as the non-linked switching partial area, an area including at least a part of a region of interest in a tomogram displayed in a display area in which the non-linked switching partial area is to he set.

2. The image display apparatus, as defined in claim 1, wherein the processor is further configured to display a boundary of the set non-linked switching partial area on the display screen.

3. A non-transitory computer-readable recording medium having stored therein an image display program for causing a computer to perform the following functions:
    obtain a tomogram from each of two or more image groups each including a series of tomograms, and between which tomograms are related to each other;
    display the obtained tomograms arranged on a display screen;
    set a linked switching partial area and a non-linked switching partial area in at least one of the plurality of display areas in which the tomograms are displayed and an input operation is to be received by an input operation receiving unit;
    when the input operation received by the input operation receiving unit has been performed in the non-linked switching partial area, switch only the tomogram displayed in the display area in which the input operation has been performed to a tomogram succeeded by or succeeding the displayed tomogram in the same image group;
    when the input operation received by the input operation receiving unit has been performed in the linked switching partial area, switch the tomogram displayed in the display area in which the input operation has been performed to the tomogram succeeded by or succeeding the displayed tomogram in the same image group and also switch the tomogram displayed in each of the other display area or areas to a tomogram that is included in the same image group as the tomogram displayed in each of the other display area or areas and related to the tomogram displayed after switching in the display area in which the input operation has been performed; and
    set, as the non-linked switching partial area, an area including at least a part of a region of interest in a tomogram displayed in a display area in which the non-linked switching partial area is to be set.

4. The non-transitory computer-readable recording medium, as defined in claim 3, wherein the program further causes the computer to display a boundary of the set non-linked switching partial area on the display screen.

* * * * *